(12) United States Patent
Shibata et al.

(10) Patent No.: US 10,456,035 B2
(45) Date of Patent: Oct. 29, 2019

(54) OPHTHALMIC SURGICAL MICROSCOPE

(71) Applicant: NIDEK CO., LTD., Gamagori-shi, Aichi (JP)

(72) Inventors: Takayoshi Shibata, Gamagori (JP); Michihiro Takii, Nukata-gun (JP); Shinya Iwata, Nukata-gun (JP)

(73) Assignee: NIDEK CO., LTD., Gamagori (JP)

( * ) Notice: Subject to any disclaimer, the term of this patent is extended or adjusted under 35 U.S.C. 154(b) by 131 days.

(21) Appl. No.: 15/687,156

(22) Filed: Aug. 25, 2017

(65) Prior Publication Data
US 2018/0055356 A1 Mar. 1, 2018

(30) Foreign Application Priority Data

Aug. 30, 2016 (JP) .................. 2016-168595

(51) Int. Cl.
| | |
|---|---|
| *A61B 3/00* | (2006.01) |
| *A61B 3/13* | (2006.01) |
| *H04N 13/239* | (2018.01) |
| *H04N 13/296* | (2018.01) |
| *H04N 13/398* | (2018.01) |
| *G02B 21/00* | (2006.01) |

(Continued)

(52) U.S. Cl.
CPC ............ *A61B 3/132* (2013.01); *A61B 3/0041* (2013.01); *G02B 21/0012* (2013.01); *G02B 21/22* (2013.01); *G02B 21/24* (2013.01); *G02B 21/365* (2013.01); *G02B 21/367* (2013.01); *G02B 21/368* (2013.01); *H04N 13/239* (2018.05); *H04N 13/296* (2018.05); *H04N 13/398* (2018.05)

(58) Field of Classification Search
CPC .... A61B 3/132; A61B 3/0041; H04N 13/296; H04N 13/398; H04N 13/239; G02B 21/22; G02B 21/368; G02B 21/24; G02B 21/365; G02B 21/367; G02B 21/0012
USPC ......................................... 348/46
See application file for complete search history.

(56) References Cited

U.S. PATENT DOCUMENTS

| | | | |
|---|---|---|---|
| 6,348,994 B1 * | 2/2002 | Geier .................. | G02B 21/22 |
| | | | 359/465 |
| 2009/0054765 A1 * | 2/2009 | Namii .................. | A61B 90/36 |
| | | | 600/425 |

(Continued)

FOREIGN PATENT DOCUMENTS

JP 2014-000159 A 1/2014

*Primary Examiner* — Jared Walker
(74) *Attorney, Agent, or Firm* — Oliff PLC

(57) ABSTRACT

An ophthalmic surgical microscope includes an observation optical system configured to guide observation luminous fluxes for a right eye and a left eye from an observation object to an imaging device, an actuator configured to move a position of the observation optical system in at least a direction intersecting with the observation luminous fluxes, a processor, and a memory storing computer-readable instructions. The computer readable instructions, when executed by the processor, cause the ophthalmic surgical microscope to cause a stereoscopic image display to display an observation image to be observed with a right eye of a user and an observation image to be observed with a left eye of the user, detect a position of the observation object with respect to the observation optical system, and correct a deviation in a relative position of the observation optical system with respect to the observation object.

6 Claims, 11 Drawing Sheets

(51) Int. Cl.
  *G02B 21/22* (2006.01)
  *G02B 21/36* (2006.01)
  *G02B 21/24* (2006.01)

(56) References Cited

U.S. PATENT DOCUMENTS

2015/0085252 A1\* 3/2015 Fujimura ................. A61B 3/15
                                                    351/208
2016/0295199 A1\* 10/2016 Takao ..................... A61B 90/20

\* cited by examiner

OPHTHALMIC SURGICAL MICROSCOPE

CROSS REFERENCE TO RELATED APPLICATION

This application is based upon and claims the benefit of priority of Japanese Patent Application No. 2016-168595 filed on Aug. 30, 2016, the contents of which are incorporated herein by reference in its entirety.

BACKGROUND

The present disclosure relates to ophthalmic surgical microscope.

A surgical microscope is known that allows a user (such as a surgeon) to observe a biological object during surgery. For example, with a known ophthalmic surgical microscope, an observation unit and an illumination unit are positioned with respect to an observation object, by a surgeon operating an alignment operation portion. As a result, the user can observe a preferred position. The observation object is observed through left and right eyepieces.

SUMMARY

When a biological object is observed with a surgical microscope, there is a case in which the biological object moves during observation, and as a result, the observation position deviates from the preferred position. With a conventional surgical microscope, the observation position can be corrected by the user performing various operations. However, performing various operations during surgery is troublesome for the user. Also, it is conceivable to automatically correct the position of an observation unit in response to movement of the observation object. However, if the position of the observation unit moves automatically, the position of the eyepieces provided on the observation unit may deviate from the user's line of sight. In this case, the user may lose sight of the observation field. Therefore, with a conventional surgical microscope, it is difficult for a user to properly observe an observation object, regardless of movement of the biological object.

Embodiments of the broad principles derived herein provide an ophthalmic surgical microscope that enables a user to properly observe an observation object regardless of movement of a biological object.

Embodiments provide an ophthalmic surgical microscope that includes an observation optical system, an actuator, a processor, and a memory. The observation optical system is configured to guide an observation luminous flux for a right eye and an observation luminous flux for a left eye from an observation object to an imaging device. The actuator is configured to move a position of the observation optical system in at least a direction intersecting with the observation luminous flux for the right eye and the observation luminous flux for the left eye. The memory stores computer-readable instructions. The computer readable instructions, when executed by the processor, cause the ophthalmic surgical microscope to cause a stereoscopic image display to display an observation image to be observed with a right eye of a user and an observation image to be observed with a left eye of the user, on the basis of an image signal from the imaging device, detect a position of the observation object with respect to the observation optical system, and correct a deviation in a relative position of the observation optical system with respect to the observation object, by causing the actuator to operate on the basis of a detection result of the position.

DETAILED DESCRIPTION

Overview

Figure 1:
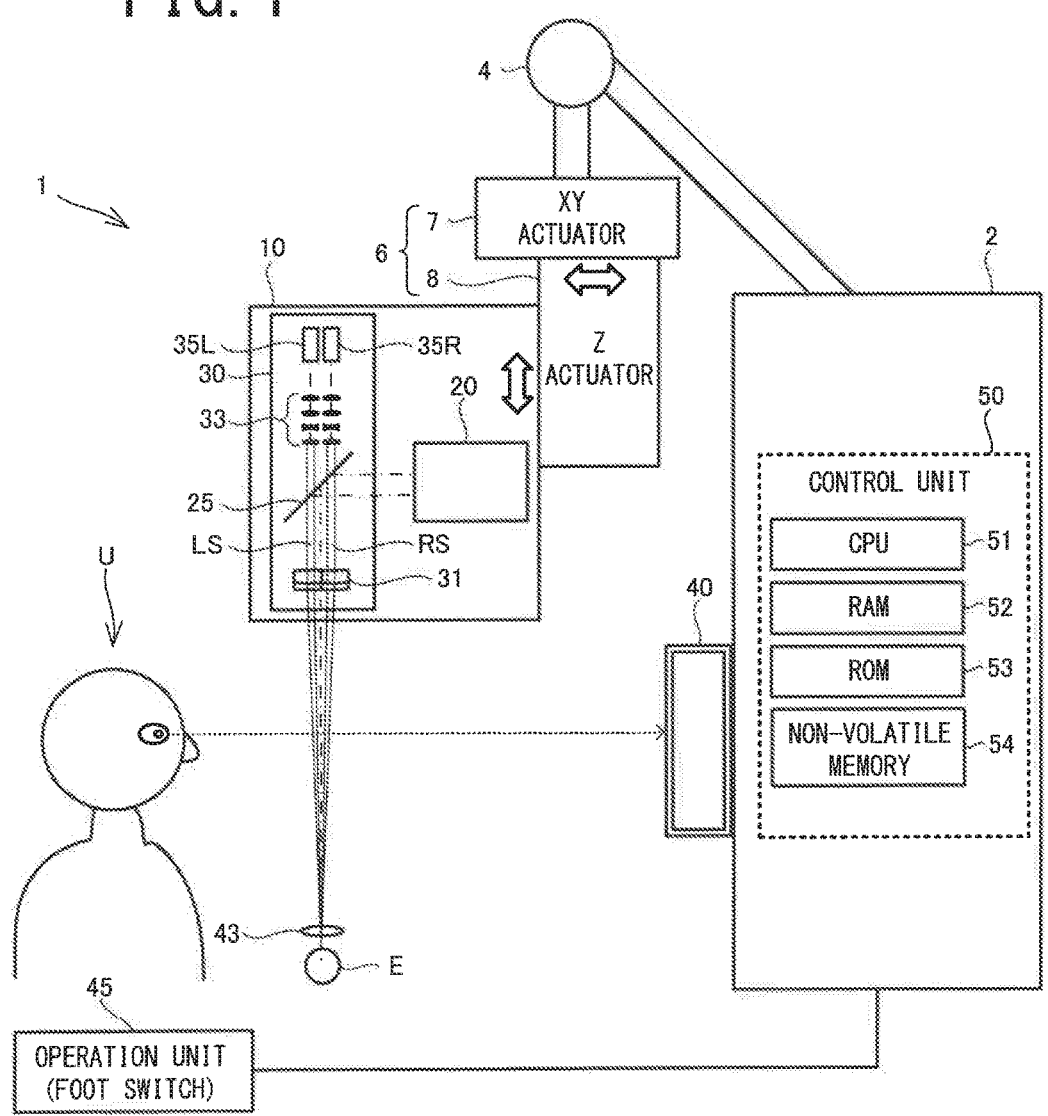
FIG. 1 is a view of the general configuration of a surgical microscope 1.

A surgical microscope exemplified in the present disclosure includes an observation optical system, an actuator, and a processor. The processor is configured to perform control of the surgical microscope. The observation optical system is configured to guide an observation luminous flux for a right eye and an observation luminous flux for a left eye from an observation object to an imaging device. The actuator is configured to move a position of the observation optical system in at least a direction intersecting with the observation luminous flux for the right eye and the observation luminous flux for the left eye. The processor is configured to cause a stereoscopic image display to display an observation image to be observed with a right eye of a user and an observation image to be observed with a left eye of the user, on the basis of an image signal from the imaging device. The processor is also configured to detect a position of the observation object with respect to the observation optical system. The processor is further configured to correct a deviation in a relative position of the observation optical system with respect to the observation object, by causing the actuator to operate on the basis of a detection result of the position.

In this case, even if a biological object that is an observation object moves, the user can observe its appropriate position without performing a fine operation of an operation unit or the like. Further, the user can stereoscopically view the observation object by looking at a stereoscopic image display. Therefore, unlike a case where the observation object can be observed only through an eyepiece, the user can constantly observe the appropriate position without moving the user's line of sight or face in accordance with the movement of an observation optical system. Thus, the user can appropriately observe the observation object regardless of movement of the biological object.

The processor may correct a deviation in the relative position by causing the observation optical system to rotate around an axis parallel to the observation luminous flux, in addition to causing the observation optical system to move in a direction that intersects with the observation luminous flux for the right eye and the observation luminous flux for the left eye. In this case, the deviation in the relative position can be more appropriately corrected.

The processor may correct the deviation in the relative position by causing the actuator to operate, in response to determining that a condition for correcting the deviation in the relative position is satisfied. When an automatic position correction is always executed each time an observation object comes out of position with respect to the observation optical system, the user looking at the observation image may feel odd. For example, when a biological object moves while a user has fixed a surgical instrument, if the automatic position correction is always executed in accordance with the movement of the biological object, it may appear to the user that the surgical instrument supposed to be fixed is moving. Also, when the user intentionally moves the biological object to change the observation position, the automatic position correction would be against the intention of the user. However, the processor may correct a deviation in the relative position when a specified condition is satisfied. In this case, the user can properly observe the observation object, while the likelihood of the user feeling odd can be reduced.

The processor may execute the automatic position correction on the condition that the position deviation of the observation object with respect to the observation optical system exceeds an allowable range. In this case, the automatic position correction is not executed when the movement of the observation object is small and the position deviation is within the allowable range. Therefore, the likelihood of the user feeling odd by an unnecessary automatic position correction can be reduced.

The processor may change the allowable range in accordance with a magnification (a display magnification) of a captured image of the observation object displayed on the stereoscopic image display. As an example, the processor may change the allowable range such that the allowable range of position deviation becomes smaller as the display magnification becomes larger. When the display magnification is large, the display region tends to fluctuate with even the slight deviation in the relative position. Conversely, when the display magnification is small, the region desired by the user is likely to be continuously displayed on the stereoscopic image display if the deviation in the relative position is small. Therefore, the position deviation can be more appropriately corrected by changing the allowable range of the position deviation in accordance with the display magnification.

The processor may execute the automatic position correction on the condition that a command to correct the deviation in the relative position is input. In this case, the user may input the command only when the automatic position correction is necessary. Therefore, the user does not feel odd because of an unnecessary automatic position correction. Also, an automatic position correction in accordance with the detection result is executed just by the user inputting the command, when it is necessary to correct a position deviation. Accordingly, a deviation in the relative position can be suitably corrected without the user performing a complex operation.

The processor may cause a supplemental image to be displayed superimposed on a captured image of the observation object displayed on the stereoscopic image display. The supplemental image may be an image used to assist a user with surgery on a biological object being the observation object. The processor may further correct a position where the supplemental image is imposed on the captured image of the observation object, on the basis of the detection result of the position of the observation object. In this case, the supplemental image can be displayed superimposed at a more suitable position.

Also, the processor may execute both control that corrects a deviation in the relative position of the observation object and the observation optical system only when a specified condition is satisfied and control that corrects the superimposed position of the supplemental image. In this case, the supplemental image can be displayed superimposed at a suitable position even while the specified condition is not satisfied and a deviation in the relative position of the observation object and the observation optical system is not corrected.

The processor may detect the relative position of the observation object and the observation optical system, by detecting, through image processing, a position of one of an optical element and a surgical instrument, in an image captured by the imaging device. The one of the optical element and the surgical instrument may be arranged in a fixed position with respect to the observation object. In this case, the relative position can be more appropriately detected.

However, the method for detecting the relative position may be modified. For example, the processor may detect the relative position by detecting, through image processing, the position of a specific portion (in the case of an ophthalmic surgical microscope, at least one of a corneal limbus, a pupil, a iris, a optic disc, a macular region, a fundus oculi blood vessel, and the like of a patient's eye, for example) of a biological object, which is an observation object, in an image captured by an imaging device. The relative position may be detected by detecting, through image processing, the position of a mark applied to the biological object by the user. Also, the processor may detect the relative position by detecting the position of a bright spot (in the case of an ophthalmic surgical microscope, a Purkinje image or the like that appears because of reflection from the cornea, for example) that appears because of illumination light reflected by the biological object, in the captured image. In these cases, the processor may detect the relative position by matching the position of the bright spot or the characteristic portion of the biological object with coordinates on the imaging device.

Also, the processor may detect the relative position on the basis of a correlative relationship between a reference image captured when the position of the observation object is an appropriate position and a current image captured in real time (a real-time image). In this case, the processor may, for example, calculate a correlation value of the reference image and the real-time image using a method such as a phase-only correlation method and detect the relative position on the basis of the calculated correlation value.

Also, the processor may detect the relative position on the basis of the relationship between a total viewing field region that is the entire region observable with the observation luminous flux and a display viewing field region that is the region, of the total viewing field region, that is actually displayed on the stereoscopic image display.

Also, the processor may detect the relative position without using an image captured by the imaging device. For example, the processor may detect the relative position on the basis of an optical coherence tomography (OCT) signal for obtaining a tomographic image or the like of a biological object.

The observation optical system may guide the observation luminous flux for the right eye of the user to a right eye imaging device, and guide the observation luminous flux for the left eye of the user to a left eye imaging device. The processor may cause the stereoscopic image display to display an observation image to be observed with the right eye of the user, on the basis of an image signal from the right eye imaging device, and cause the stereoscopic image display to display an observation image to be observed with the left eye of the user, on the basis of an image signal from the left eye imaging device. In this case, the user can properly stereoscopically view the observation object regardless of movement of the biological object.

The processor may receive an input of a command to specify a reference position. The reference position may a position serving as a reference for correcting the deviation in the relative position. The processor may correct the deviation in the relative position of the observation object with respect to observation optical system, by causing the actuator to operate to bring the relative position closer to the reference position. In this case, the user can properly observe a desired region regardless of movement of the biological object, by specifying the reference position such that the desired region is displayed on the stereoscopic image display.

However, the reference position may be determined in advance. For example, in the case of an ophthalmic surgical microscope, the relative position in which the center position of the pupil is the center of the display region of the stereoscopic image display may be set in advance as the reference position.

EMBODIMENTS

Hereinafter, an exemplary embodiment of the present disclosure will be described with reference to the drawings. This embodiment illustrates an ophthalmic surgical microscope 1 for stereoscopically viewing a patient's eye during eye surgery. However, at least a portion of the technology illustrated in this embodiment can also be applied to a surgical microscope used for a purpose other than ophthalmology. As shown in FIG. 1, the surgical microscope 1 of the embodiment includes a base unit 2, an arm unit 4, an actuator (a moving unit) 6, an observation device 10, and an operation unit 45.

The base unit 2 is a portion that serves as the base of the surgical microscope 1. In this embodiment, a control unit 50, which is described below, is built into the base unit 2. The arm unit 4 has at least one joint, and movably supports the observation device 10. In this embodiment, a proximal portion of the arm unit 4 is connected to the base unit 2, and a distal end portion of the arm unit 4 is connected to the actuator 6. The user can manually move the position of the observation device 10 by moving the joint of the arm unit 4.

The actuator 6 moves the position of the observation device 10, which includes an observation optical system 30. As an example, the actuator 6 of the embodiment includes an XY actuator (an XY moving unit) 7 and a Z actuator (a Z moving unit) 8. The XY actuator 7 is connected to the arm unit 4 and the Z actuator 8. Furthermore, the observation device 10 is connected to the Z actuator 8. An XY moving motor (not shown in the drawings) is provided in the XY actuator 7. A Z moving motor (not shown in the drawings) is provided in the Z actuator 8. When the control unit 50 causes the XY moving motor to operate, the Z actuator 8 and the observation device 10 move in a direction (the XY direction) that intersects with observation luminous fluxes RS and LS. When the control unit 50 causes the Z moving motor to operate, the observation device 10 moves in a direction (the Z direction) that is along the optical axes of the observation luminous fluxes RS and LS. The configuration of the actuator 6 may be modified. For example, a rotating mechanism may be used for the XY actuator. The Z actuator, which moves the observation device 10 in the Z direction, may be omitted.

The observation device 10 includes an illumination optical system 20, a beam splitter 25, and an observation optical system 30. The illumination optical system 20 emits illumination light that illuminates a biological object (a patient's eye E in this embodiment) that is an observation object. As an example, in this embodiment, a technology called red reflex is employed that, when cataract surgery is performed, forms an image of an illumination light source of the illumination optical system 20 on the ocular fundus of the patient's eye E and bright-field illuminates the crystalline lens with a red color derived from the blood vessels of the ocular fundus. The illumination optical system 20 is capable of emitting illumination light coaxial with the optical axis of the observation luminous flux RS for the right eye in the observation optical system 30 and illumination light coaxial with the optical axis of the observation luminous flux LS for the left eye in the observation optical system 30. However, the illumination light may be irradiated toward the observation object from an angle that differs from the optical axis of the observation luminous fluxes RS and LS.

The observation luminous fluxes RS and LS in this embodiment refer to luminous fluxes guided by the observation optical system 30 to produce light to be observed by the user U, of the luminous fluxes from the observation object (e.g., the luminous fluxes of the illumination light reflected by the observation object).

The beam splitter 25 is one example of an optical axis coupling element that makes the optical axis of the illumination light emitted by the illumination optical system 20 and the optical axes of the observation luminous fluxes RS and LS in the observation optical system 30 coaxial. The beam splitter 25 illustrated in FIG. 1 makes the optical axis of the illumination light and the optical axes of the observation luminous fluxes RS and LS coaxial by reflecting at least a portion of the illumination light emitted from the illumination optical system 20 and transmitting at least a portion of the observation luminous fluxes RS and LS from the observation object. The illumination light reflected by the beam splitter 25 travels along the same optical path as part of the optical path of the observation luminous fluxes RS and LS, in a direction opposite to the direction in which the observation luminous fluxes RS and LS travel, and is irradiated on the observation object. Illumination light may be guided toward the observation object by an optical element (a prism or a partial reflection mirror, for example) other than the beam splitter 25.

The observation optical system 30 guides the observation luminous flux from the observation object to allow the user to observe (stereoscopically view, in this embodiment) the observation object. The surgical microscope 1 in this embodiment allows the user U to stereoscopically view the observation object by causing a display (a stereoscopic image display in this embodiment) 40 to display an observation image to be observed with the right eye of the user U and an observation image to be observed with the left eye of the user U. Therefore, the observation optical system 30 guides the right eye observation luminous flux RS from the observation object to a right eye imaging device 35R, and guides the left eye observation luminous flux LS from the observation object to a left eye imaging device 35L. The control unit 50 controls the image display of the display 40 on the basis of image signals from the two imaging devices 35R and 35L. Any of various kinds of displays, such as a three-dimensional display, a stereo viewer, and a head mounted display, for example, may be used for the display to cause stereoscopic vision of the observation object. There is no need to separately provide the right eye imaging device 35R, to which the right eye observation luminous flux RS is guided, and the left eye imaging device 35L, to which the left eye observation luminous flux LS is guided. For example, an area to which the right eye observation luminous flux RS is guided and an area to which the left eye observation luminous flux LS is guided may be provided in an imaging area of a single imaging device.

The observation optical system 30 includes an objective lens 31, a lens group 33, and the imaging devices 35R and 35L described above. In this embodiment, a front focal point of the objective lens 31 is on the object surface of the observation object, when a front lens 43 or the like, which is described below, is not provided. In this case, the observation luminous fluxes RS and LS from the observation object that are at the front focal point of the objective lens 31 are formed into parallel luminous fluxes by the objective lens 31, and guided to the lens group 33. The objective lens 31 may be a finite conjugate system that emits the observation luminous fluxes RS and LS that are not parallel luminous fluxes toward the downstream side and focuses the observation luminous fluxes RS and LS into an image. The lens group 33 guides the observation luminous fluxes RS and LS emitted from the objective lens 31 to the imaging devices 35R and 35L. In this embodiment, at least one of the lenses in the lens group 33 are moved in the optical axis direction of the observation luminous fluxes RS and LS. As a result, the magnification of the observation image displayed on the display 40 changes. Also, the surgical microscope 1 in this embodiment can change the magnification when causing the display 40 to display an observation image captured by the imaging devices 35R and 35L. Thus, the surgical microscope 1 can optically change the magnification of a captured image and electronically change the magnification of the image displayed on the display 40, by moving the lens group 33. Although a diaphragm and the like is also provided in the optical path of the observation luminous fluxes RS and LS in the observation optical system 30, a description thereof will be omitted.

The example illustrated in FIG. 1 illustrates a case in which a wide-angle observation unit for allowing the user to observe the ocular fundus of the patient's eye E at a wider angle is used. It is useful to use a wide-angle observation unit in vitreous surgery, for example. In the example illustrated in FIG. 1, the front lens 43 arranged in a fixed position with respect to the patient's eye E, which is the biological object, is shown as a part of the wide-angle observation unit.

The observation optical system 30 may include a configuration for allowing the user U to stereoscopically view the observation object by looking through eyepieces. In this case, the observation optical system 30 may guide the right eye observation luminous flux RS to an eyepiece for the right eye of the user U and guide the left eye observation luminous flux LS to an eyepiece for the left eye of the user U.

The operation unit 45 may be operated by the user U to input various operation commands into the surgical microscope 1. In this embodiment, a foot switch, which is operated by a foot of the user U, is at least provided as the operation unit 45. Therefore, the user U can input various operation commands from the foot switch 45, while handling a surgical instrument with the user's hand. However, another device (various buttons or a touch panel, for example) may be used as the operation unit 45, together with the foot switch, or instead of the foot switch.

The control unit 50 controls various operations of the surgical microscope 1. The control unit 50 includes a CPU 51, a RAM 52, a ROM 53, and a non-volatile memory 54. The CPU 51 is a controller that performs various types of control. The RAM 52 temporarily stores various kinds of information. The ROM stores programs to be executed by the CPU 51, various initial values, and the like. The non-volatile memory 54 is a non-transitory storage medium capable of retaining stored content even when the supply of power is cut off. The non-volatile memory 54 may store a position correction processing program for executing a position correction processing (see FIG. 2), which is described below. In this embodiment, the control unit 50 executes, for example, display control of the display 40 based on the image signals from the imaging devices 35R and 35L, drive control of the actuator 6, and processing of operation signals inputted from the operation unit 45, and the like. At least a part of these pieces of processing may be executed by a control unit of a device (for example, a personal computer connected to a surgical microscope) other than the surgical microscope 1.

The position correction processing executed by the surgical microscope 1 in this embodiment will now be described with reference to FIG. 2 to FIG. 11. In the position correction processing, a deviation of the relative position of the observation object and the observation optical system 30 is corrected on the basis of a detection result regarding the position of the observation object with respect to the observation optical system 30. The CPU 51 of the control unit 50 executes the position correction processing illustrated in FIG. 2, in accordance with the position correction processing program stored in the non-volatile memory 54.

First, the CPU 51 receives an input of a selection command for a position correction mode (S1). In this embodiment, the user may operate the operation unit 45 or the like to select any one of four position correction modes: a continuous automatic mode, a conditional automatic mode, a specified timing correction mode, and position correction OFF. The continuous automatic mode is a mode in which a position deviation is continuously corrected when there is a deviation in the relative position of the observation object and the observation optical system 30 (hereinafter also referred to as the "relative position"). The conditional automatic mode is a mode in which a position deviation is corrected on the condition that a deviation of the relative position exceeds an allowable range. The specified timing correction mode is a mode in which a position deviation is corrected on the condition that an execution command for a position correction is input by the user. Position correction OFF is a mode in which an automatic position correction is not performed by the control unit 50. The user can select an appropriate position correction mode in accordance with the type of surgery to be performed, and the like.

The CPU 51 executes one of the position correction modes, in accordance with the selection command by the user (S2 to S7). When position correction OFF is selected (NO in S6), a position correction is not performed (S8). Hereinafter, continuous auto-correction processing, conditional auto-correction processing, and specified timing correction processing will be described in detail.

The continuous auto-correction processing will be described with reference to FIG. 3. In the continuous auto-correction processing, first it is determined whether a command to specify a reference position has been input (S21). The reference position is a relative position that serves as a reference for correcting a deviation in the relative position of the observation object and the observation optical system 30. The CPU 51 corrects a deviation of the relative position by causing the actuator 6 to operate to bring the relative position of the observation object and the observation optical system 30 closer to the reference position. Therefore, the relative position desired by the user (specifically, the relative position where the user can appropriately observe the desired position of the observation object) is generally used as the reference position. When the command to specify the reference position is input (YES in S21), the CPU 51 sets the specified relative position as the reference position (S22). In this embodiment, a default reference position at the time when the position correction processing starts is set in advance. Unless a command is input by the user, the default reference position will be set as it is.

Figure 4:
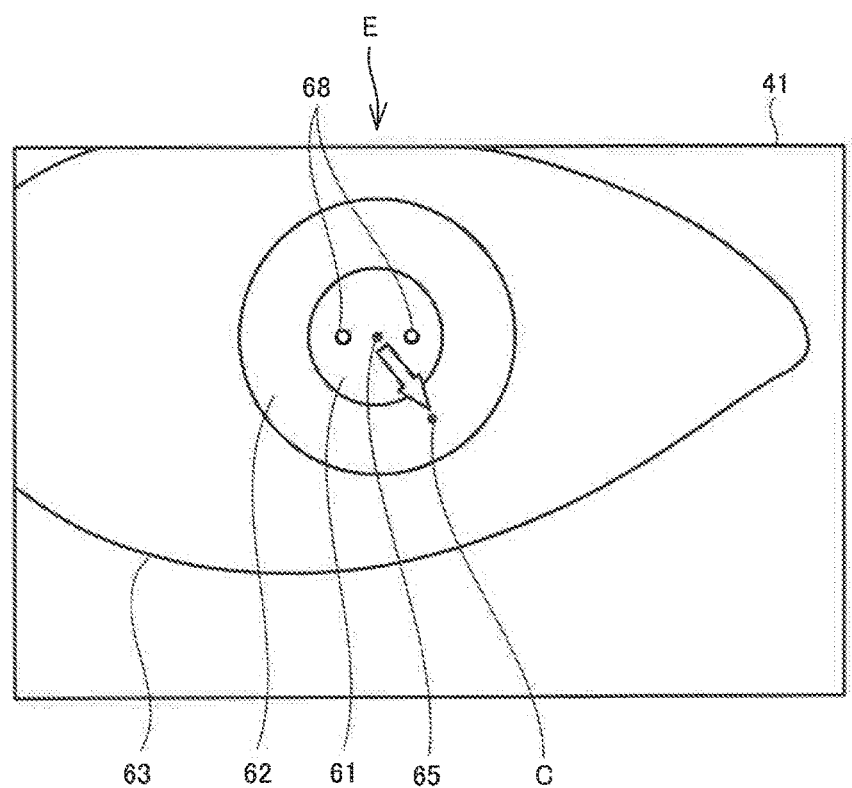
FIG. 4 is an explanatory view illustrating an example of a method for correcting a position while an image of an anterior ocular segment of a patient's eye E is being captured.

One example of a method for setting the reference position will be described with reference to FIG. 4. In FIG. 4, a pupil 61, an iris 62, an eyelid 63, and the like of the patient's eye E are included in a captured image displayed in a display region 41 of the display 40. Purkinje images 68 that appear because of illumination light reflected by the cornea of the patient's eye E are also included in the captured image.

Here, a case in which the user specifies the relative position of the observation object (the patient's eye E) and the observation optical system 30 as the reference position, when the center 65 of the pupil 61 is the center C of the image capture range of the imaging devices 35R and 35L, will be illustrated. For example, the user may input a specified command for the reference position while the center 65 of the pupil 61 is positioned in the center C of the image capture range. In this case, the CPU 51 detects the position of the center 65 of the pupil 61 as a reference site by processing an image (hereinafter referred to as a "reference image") captured when the command is input, and detecting the outline of the pupil 61. The CPU 51 sets the relative position of the observation object and the observation optical system 30 when the reference image is captured (i.e., the relative position where the center 65 of the pupil 61 is the center of the image capture range) as the reference position, by storing the position of the reference site in the reference image.

It goes without saying that the method for setting the reference position can be modified. For example, the CPU 51 may allow the user to directly specify the site, in the captured image, to be positioned at the center C of the image capture range, by the user operating a touch panel, a mouse, direction keys, or the like. The CPU 51 may move the reference position in the XY direction in accordance with the user's operation of the direction keys or the like. It goes without saying that a site other than the center 65 of the pupil 61 (the entire region of the pupil 61, the outline of the pupil 61, the center of the iris 62, the corneal limbus, or the outline of the eyelid 63, for example) may be used as the reference site. The position where a Purkinje image 68 appears may be set as the reference site. The position of a mark applied to the biological object by the user may be used as the reference site.

Figure 5:
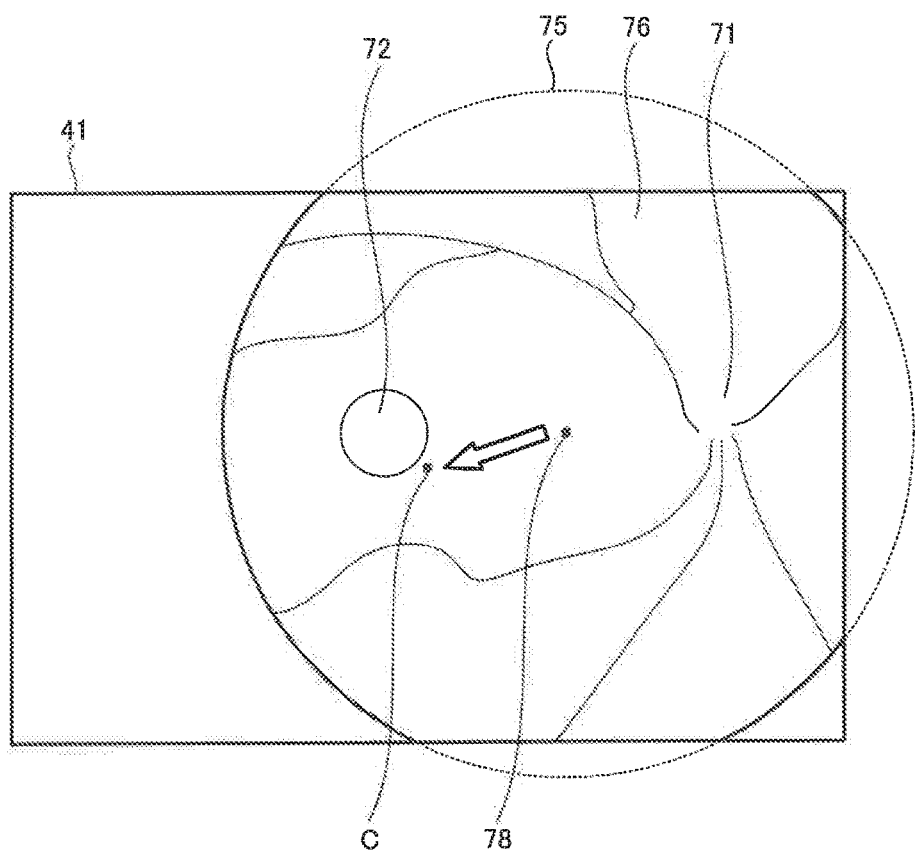
FIG. 5 is an explanatory view illustrating an example of a method for correcting a position while an image of an ocular fundus of the patient's eye E is being captured.

Another example of a method for setting the reference position will be described with reference to FIG. 5. In FIG. 5, a captured image that includes an optic disc 71, a macula 72, fundus oculi blood vessels, and the like of the ocular fundus of the patient's eye E is displayed in the display region 41 during vitreous surgery. In the example illustrated in FIG. 5, only a portion of a total viewing field region 75 that is the entire region observable with the observation luminous fluxes RS and LS is displayed as a display viewing field region 76. In this embodiment, the outline of the total viewing field region 75 is determined by an outer peripheral edge portion of the front lens 43 (see FIG. 1) arranged in a fixed position with respect to the patient's eye E, or an inner peripheral edge portion of the iris 62 of the patient's eye E.

As an example, the CPU 51 detects a portion of the outline of the total viewing field region 75 displayed in the display region 41, by processing the captured image. The CPU 51 calculates the entire outline of the total viewing field region 75, including the portion that is not displayed, based on the detected portion of the outline. Next, the CPU 51 detects the position of the center 78 of the total viewing field region 75 as the reference site, based on the entire outline of the total viewing field region 75. In the example illustrated in FIG. 5, the relative position of the observation object and the observation optical system 30, when the center 78 of the total viewing field region 75 serves as the center C of the image capture range, is set as the default reference position at the start of the position correction processing. The CPU 51 can move the reference position in the XY direction in accordance with the user's operation of the direction keys or the like.

It goes without saying that a site other than the center 78 of the total viewing field region 75 (at least a portion of the outline of the total viewing field region 75, the optic disc 71, the macula 72, or a fundus oculi blood vessel, for example), may be used as the reference site.

Figure 3:
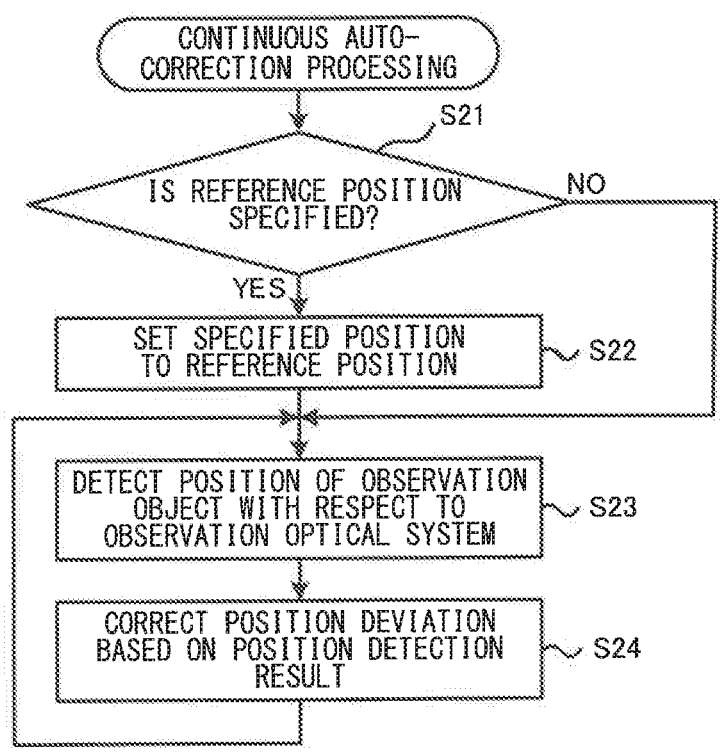
FIG. 3 is a flowchart of continuous auto-correction processing executed by the surgical microscope 1.

Returning now to the description of FIG. 3, the CPU 51 detects the relative position of the observation object with respect to the observation optical system 30 (S23). For example, in the methods illustrated in FIG. 4 and FIG. 5, the CPU 51 detects the relative position by processing an image captured in real time, and comparing the reference site in the real-time image (the center 65 of the pupil 61, or the center 78 of the total viewing field region 75), and the reference site when the observation object and the observation optical system 30 are in the reference position (when the reference site is aligned with the center C of the image capture range in FIG. 4 and FIG. 5), with the coordinates of the imaging device.

The CPU 51 in this embodiment detects the relative position by processing the image captured by the imaging devices 35R and 35L, not the image being displayed on the display 40. Therefore, when a portion of the image captured by the imaging devices 35R and 35L is enlarged on the display 40, the relative position is appropriately detected, even if the reference site is not included in the display region 41 of the display 40.

Also, the method for detecting the relative position may be modified. For example, there may be a case where an optical device (the front lens 43 in this embodiment) or a surgical instrument (a lid retractor, for example) arranged in a fixed position with respect to the observation object (the patient's eye E in this embodiment) appears in the captured image. In this case, the CPU 51 may detect the relative position of the observation object and the observation optical system 30, by detecting the position of the optical device or the surgical instrument. Also, the CPU 51 may detect the relative position on the basis of the correlative relationship between a reference image captured when the observation object and the observation optical system 30 are in the reference position, and the real-time image captured at that time. In this case, the CPU 51 may calculate a correlation value of the reference image and the real-time image using a method such as a phase-only correlation method, and detect the relative position on the basis of the calculated correlation value. Also, in the example illustrated in FIG. 5, the CPU 51 may detect the relative position on the basis of the position of the outline displayed in the display region 41, of the outline of the total viewing field region 75.

Next, the CPU 51 corrects a deviation of the relative position of the observation optical system 30 with respect to the observation object, by causing the actuator 6 to operate on the basis of the detection result of the relative position (S24). As an example, in the methods illustrated in FIG. 4 and FIG. 5, the CPU 51 brings the relative position closer to the reference position such that the reference site in the real-time image (the center 65 of the pupil 61 or the center 78 of the total viewing field region 75) approaches the reference site in the reference image (the center C of the image capture range). As a result, the observation object can be appropriately observed regardless of movement of the patient's eye E, which is the biological object. If a command to change the reference position is input by the user while the relative position detection processing (S23) and the position deviation correction processing (S24) are being performed, the CPU 51 changes the reference position to the specified position (S22), and executes the subsequent processing in S23 and S24 on the basis of the changed reference position.

The method for correcting a deviation of the relative position maybe modified. For example, in the method illustrated in FIG. 5, the actuator 6 may be operated such that a gap between the outline of the total viewing field region 75 and the outer peripheral edge of the image capture region of the imaging devices 35R and 35L is even. The CPU 51 may cause the actuator 6 to operate such that the correlation value of the reference image and the real-time image approaches the maximum value.

Further, the CPU 51 may detect both a deviation of the relative position in the XY direction that intersects with the optical axes of the observation luminous fluxes RS and LS and a deviation of the relative position in the rotational direction around an axis parallel to the optical axes. In this case, the CPU 51 may correct the deviation of the relative position in the XY direction and the deviation of the relative position in the rotational direction, by causing the actuator 6 to operate. In this case, the deviation in the relative position can be more appropriately corrected.

The conditional auto-correction processing will be described with reference to FIG. 6 to FIG. 9. As described above, in the conditional auto-correction processing, a position deviation is corrected on the condition that a deviation of the relative position exceeds an allowable range. That is, when the deviation of the relative position is within an allowable range, the automatic position correction is not executed, which keeps the user from feeling odd because of the automatic position correction being constantly performed.

Figure 7:
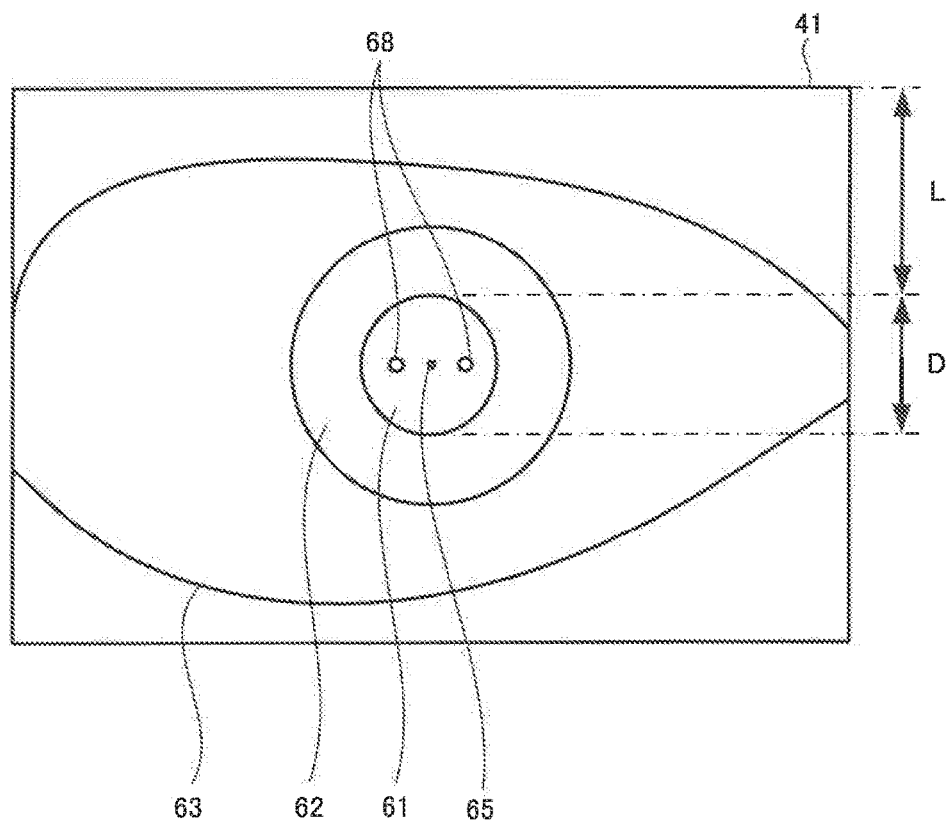
FIG. 7 is an explanatory view illustrating the conditional auto-correction processing executed while an image of the anterior ocular segment of the patient's eye E is being captured.
Figure 8:
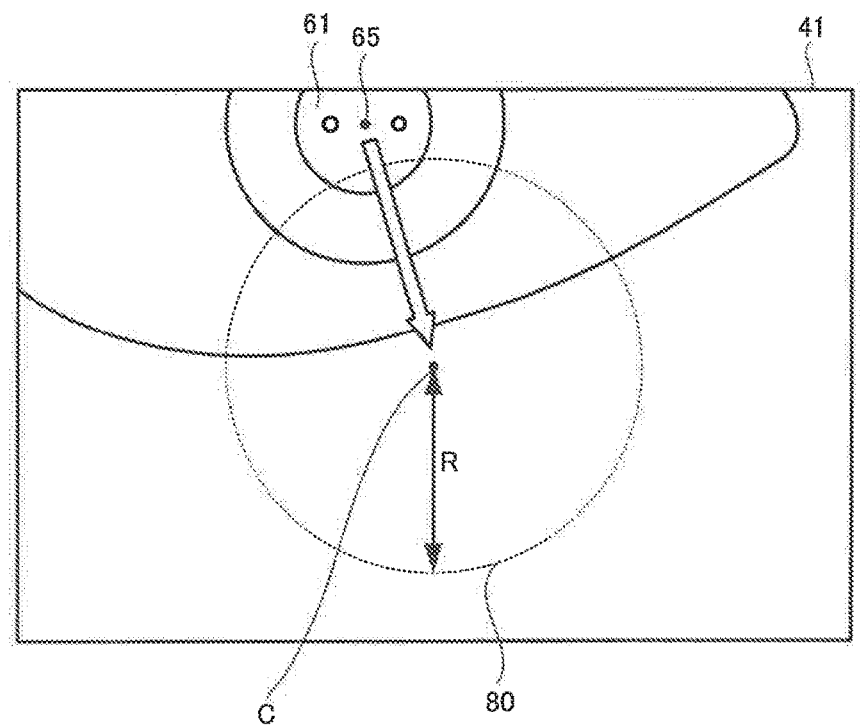
FIG. 8 is an explanatory view illustrating the conditional auto-correction processing executed while an image of the anterior ocular segment of the patient's eye E is being captured.

First, the allowable range that defines the condition for executing a position correction will be described with reference to FIG. 7 to FIG. 9. In FIG. 7 and FIG. 8, the pupil 61 and the like of the patient's eye E is shown, which is similar to FIG. 4. Here, in the example illustrated in FIG. 7 and FIG. 8, the pupil 61 of the patient's eye E is selected as the region that the user wishes to observe. In the example illustrated in FIG. 7 and FIG. 8, the narrower width of the vertical width and the horizontal width of the display region 41 is the vertical width. In this case, the CPU 51 calculates (the narrower width of the display region 41–the width D of the region that the user wishes to observe)/2=L, as illustrated in FIG. 7. As illustrated in FIG. 8, when the radius R of a circular dead zone region 80 centered around the center C of the image capture range is made to coincide with L, the pupil 61 always falls within the display region 41 if the center 65 of the pupil 61 is positioned inside the dead zone region 80. On the other hand, if the center 65 of the pupil 61 is positioned outside the dead zone region 80, at least a portion of the pupil 61 may protrude from the display region 41. Therefore, in the example illustrated in FIG. 7 and FIG. 8, the CPU 51 sets the dead zone region 80 with the radius R=L centered on the center C, and executes a position correction when the center 65 of the pupil 61, which is the reference site, is positioned outside the dead zone region 80. In other words, when the position deviation between the reference site in the real-time image and the reference site (the center C) in the reference image has exceeded the value R, the CPU 51 determines that the position deviation of the observation object with respect to the observation optical system 30 has exceeded the allowable range, and executes a position correction.

The value R may also be changed. For the reasons described above, the value R is preferably equal to or less than the value L. More preferably, the value R is equal to or less than two-thirds of the value L, and even more preferably, the value R is equal to or less than one-half of the value L. Also, in the example illustrated in FIG. 7 and FIG. 8, the size (i.e., the radius of the dead zone region 80) R of the allowable range is set based on the width D of the pupil 61, which is the region that the user wishes to observe. However, the width of the corneal limbus or the width of the eyelid 63, for example, may be used as the width D of the region that the user wishes to observe.

Figure 9:
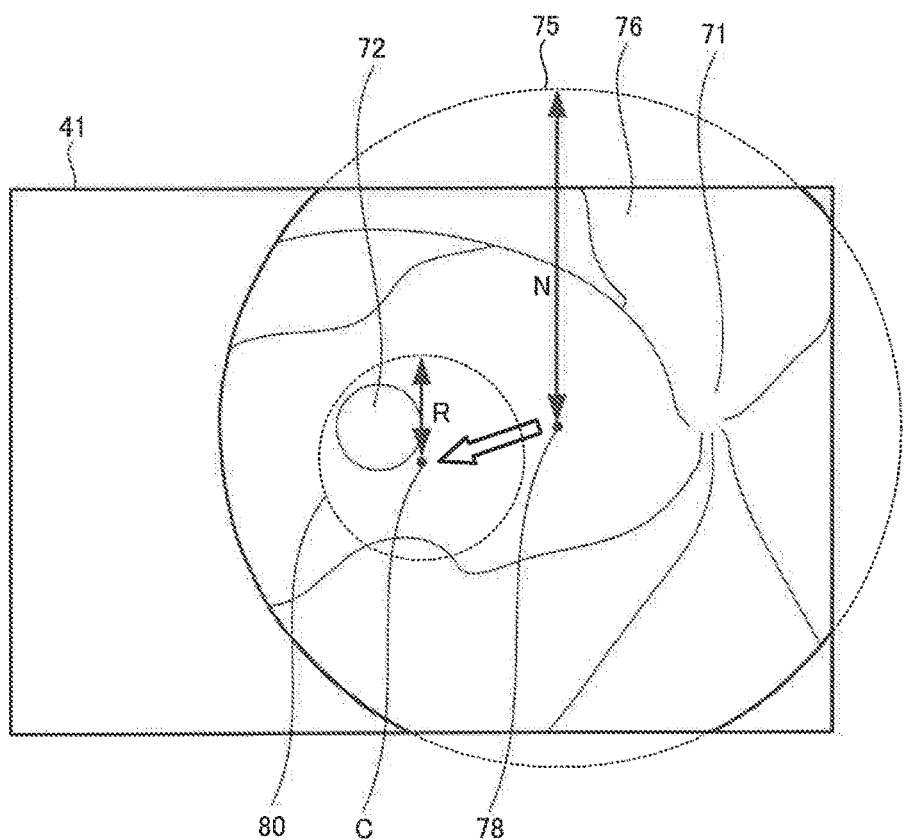
FIG. 9 is an explanatory view illustrating the conditional auto-correction processing executed while an image of the ocular fundus of the patient's eye E is being captured.

Also, FIG. 9 illustrates an example of a method for setting the size (i.e., the radius of the dead zone region 80) R of the allowable range on the basis of the radius N of the total viewing field region 75. For example, the value R is preferably equal to or less than the radius N of the total viewing field region 75, and more preferably, equal to or less than ½ of the radius N, and even more preferably, equal to or less than ¼ of the radius N.

The method for setting the allowable range may be modified. For example, the size of the allowable range may be set based on the ratio (%) of the display viewing field region 76 with respect to the area of the total viewing field region 75. In this case, when the ratio is less than T %, the CPU 51 determines that the position deviation has exceeded the allowable range, and executes a position correction. The value T is preferably equal to or greater than 50%, and more preferably, equal to or greater than 75%, and even more preferably, equal to or greater than 90%, for example. In another example, the allowable range may be set with respect to a gap between the outline of the total viewing field region 75 and an outer peripheral edge of the image capture region of the imaging devices 35R and 35L.

Figure 6:
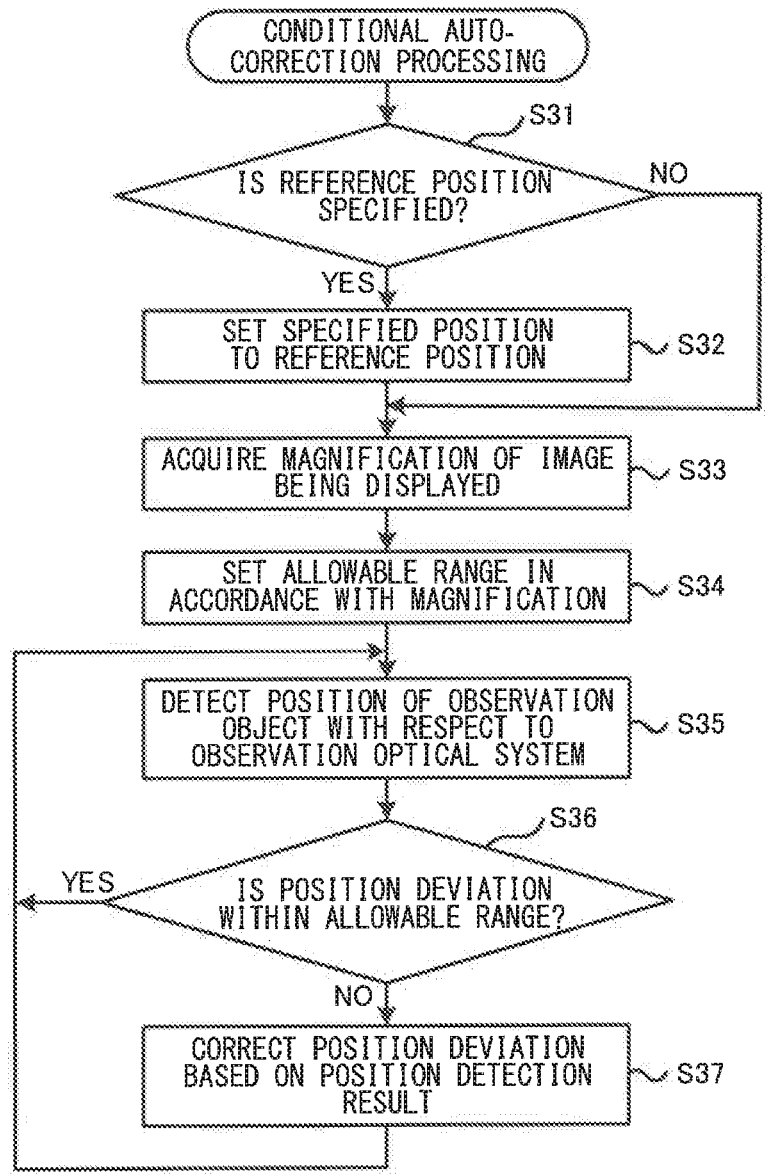
FIG. 6 is a flowchart of conditional auto-correction processing executed by the surgical microscope 1.

As illustrated in FIG. 6, the CPU 51 determines whether a command to specify a reference position has been input (S31). When a command is input (YES in S31), the specified relative position is set as the reference position (S32). Processing similar to the processing in S21 and S22 illustrated in FIG. 3 can be adopted for the processing in S31 and S32. Therefore, a description of the processing will be omitted.

Next, the CPU 51 acquires the magnification (the display magnification) of the captured image displayed on the display 40 (S33). As described above, the display magnification can be changed by at least one of an optical method and an electronic method. The CPU 51 changes the allowable range of the position deviation of the observation object with respect to the observation optical system 30, in accordance with the display magnification (S34). More specifically, the CPU 51 of this embodiment changes the allowable range such that the allowable range becomes smaller as the display magnification becomes larger. When the display magnification is large, the displayed image tends to fluctuate with even a slight deviation in the relative position. Conversely, when the display magnification is small, the region desired by the user is likely to be continuously displayed in the display region 41 if the deviation in the relative position is small. Therefore, the position deviation is more appropriately corrected by changing the allowable range in accordance with the display magnification.

Next, the CPU 51 detects the relative position of the observation object with respect to the observation optical system 30 (S35). Processing similar to the processing in S23 illustrated in FIG. 3 can be adopted for the processing of detecting the relative position in S35. Therefore, a description of this processing will be omitted. Next, the CPU 51 determines whether the detected position deviation is within the allowable range (S36). When the position deviation is within the allowable range (YES in S36), the processing returns as it is to S35 without a position correction being performed. When the position deviation exceeds the allowable range (NO in S36), the CPU 51 corrects the position deviation by causing the actuator 6 to operate on the basis of the detection result of the relative position (S37). Processing similar to the processing in S24 illustrated in FIG. 3 can be adopted for the processing of correcting the position deviation in S37. However, in S37, the CPU 51 may move the relative position to where the position deviation is completely eliminated, or may stop moving the relative position at the point at which the position deviation falls within the allowable range.

When a command to change the reference position is input by the user while the processing in S35 to S37 is being performed, the CPU 51 changes the reference position to the specified position (S32), and executes the subsequent processing in S35 to S37 on the basis of the changed reference position. When the magnification of an image being displayed is changed, the CPU 51 also changes the allowable range in accordance with the changed magnification (S33 and 834), and executes the subsequent processing of S35 to S37 on the basis of the changed allowable range.

The specified timing correction processing will now be described with reference to FIG. 10. As described above, in the specified timing correction processing, a position deviation is corrected on the condition that an execution command for a position correction is input by the user. First, the CPU 51 determines whether a command to specify a reference position has been input (S41). When a command is input (YES in S41), the specified relative position is set as the reference position (S42). Processing similar to the processing in S21 and S22 illustrated in FIG. 3 can be adopted for the processing in S41 and S42. Therefore, a description of the processing will be omitted.

Next, the CPU 51 detects the relative position of the observation object with respect to the observation optical system 30 (S43). Processing similar to the processing in S23 illustrated in FIG. 3 can be adopted for the processing of detecting the relative position in S43. Therefore, a description of the processing will be omitted. Next, the CPU 51 determines whether an execution command for a position correction has been input by the user (544). In this embodiment, the user can input an execution command for a position correction by operating the operation unit 45, which is the foot switch, with the user's foot. Therefore, the user can input an execution command for a position correction while handling a surgical instrument and the like. When an execution command has not been input (NO in S44), the processing returns as it is to S43 without a position correction being performed. When an execution command for a position correction is input (YES in S44), the CPU 51 corrects the position deviation by causing the actuator 6 to operate on the basis of the detection result of the relative position (S45). Processing similar to the processing of S24 illustrated in FIG. 3 can be adopted for the processing in S45. When a command to change the reference position is input by the user while the processing in S43 to S45 is being performed, the CPU 51 changes the reference position to the specified position (S42), and executes the subsequent processing in S43 to S45 on the basis of the changed reference position.

Figure 2:
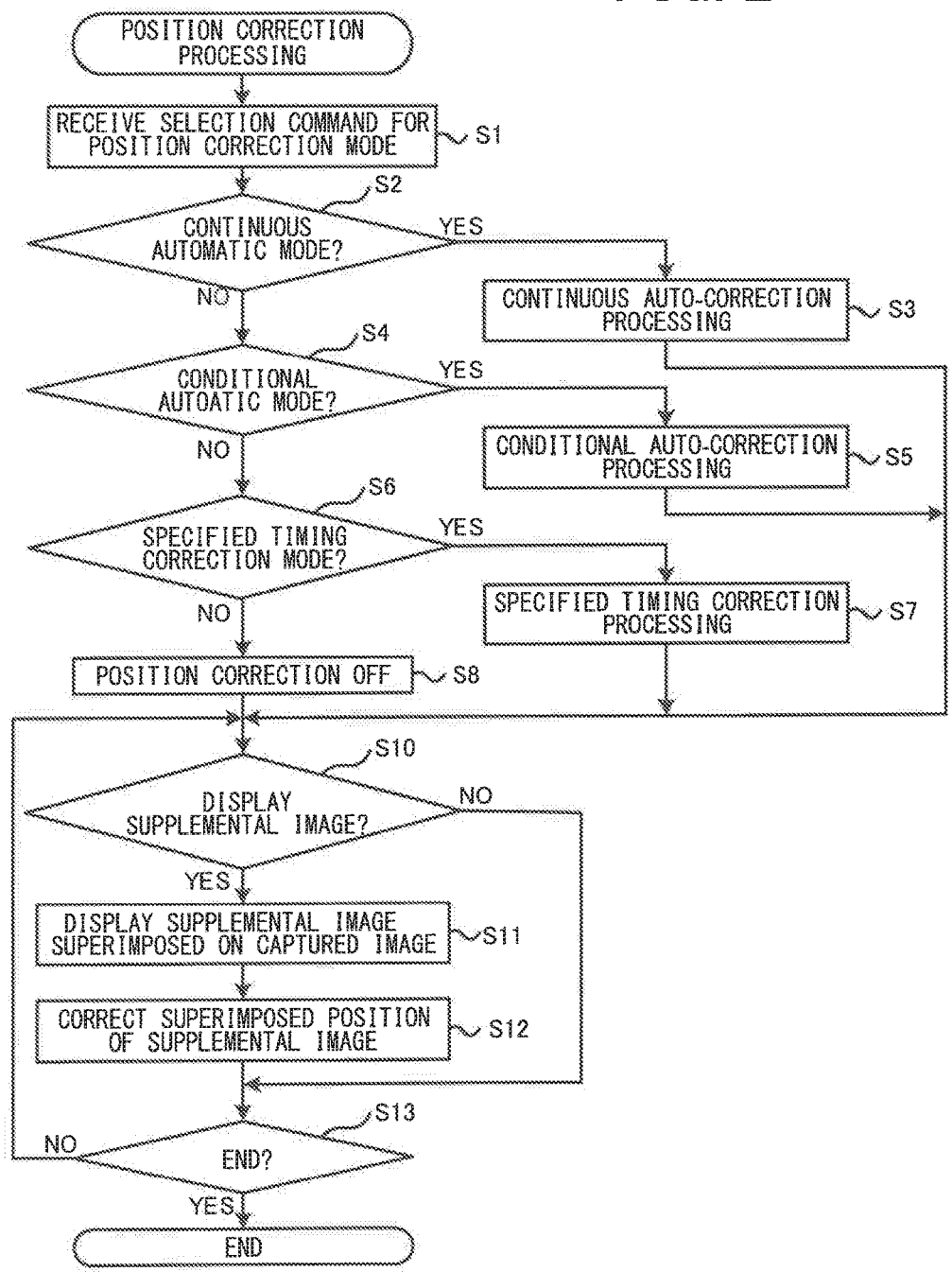
FIG. 2 is a flowchart of position correction processing executed by the surgical microscope 1.
Figure 11:
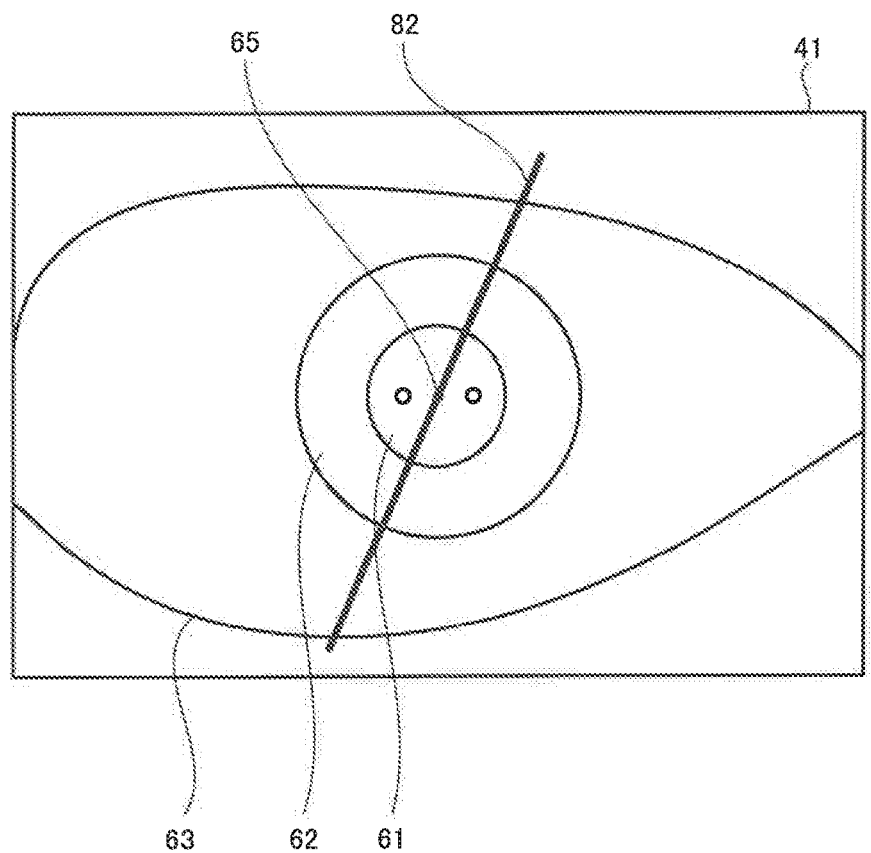
FIG. 11 is a view of an example in which a supplemental image is superimposed on a captured image of an observation object.

Returning now to the description of FIG. 2, when the processing (S1 to S8) related to correcting the relative position of the observation object and the observation optical system 30 end, the CPU 51 determines whether or not to display a supplemental image (S10). A supplemental image is an image that is displayed superimposed on the captured image of the observation object, in order to assist the user in performing surgery on the biological object. FIG. 11 illustrates an example of a supplemental image used in the ophthalmic surgical microscope 1. A straight line 82 indicating the direction of an astigmatic axis of the patient's eye E is included in the supplemental image illustrated in FIG. 11. Therefore, the user can arrange a toric intraocular lens, which is used to correct an astigmatism, in the appropriate direction, by inserting the toric intraocular lens into the patient's eye E while looking at the supplemental image. The form of the supplemental image may be modified as appropriate. For example, a circular mark for guiding to a position where an incision in the anterior capsule of the crystalline lens is to be made, a mark for guiding to a position where an incision in the cornea is to be made, or the like, may be included in the supplemental image. In this embodiment, the user may operate the operation unit 45 to select whether or not to display a supplemental image and to select the type of supplemental image to be displayed.

When a supplemental image is to be displayed (YES in S10), a supplemental image selected by the user is displayed superimposed at a specified position of the captured image of the observation object (S11). Furthermore, the position where the supplemental image is superimposed on the captured image is corrected based on the detection result of the position of the observation object with respect to the observation optical system 30 (S12). For example, in the example illustrated in FIG. 11, the supplemental image is displayed superimposed on the captured image such that the center of the straight line 82 is aligned with the center 65 of the pupil 61 (S11). Furthermore, when the biological object, which is the observation object, moves, the superimposed position of the supplemental image is corrected such that the center of the straight line 82 continues to be positioned at the center 65 of the pupil 61, based on the detection result of the position of the observation object. In the example illustrated in FIG. 11, the CPU 51 may not only correct the superimposed position of the supplemental image in the XY direction, but also correct the superimposed position of the supplemental image in the rotational direction centered around an axis parallel to the Z direction. In this case, the direction of the astigmatic axis can be more appropriately displayed.

Figure 10:
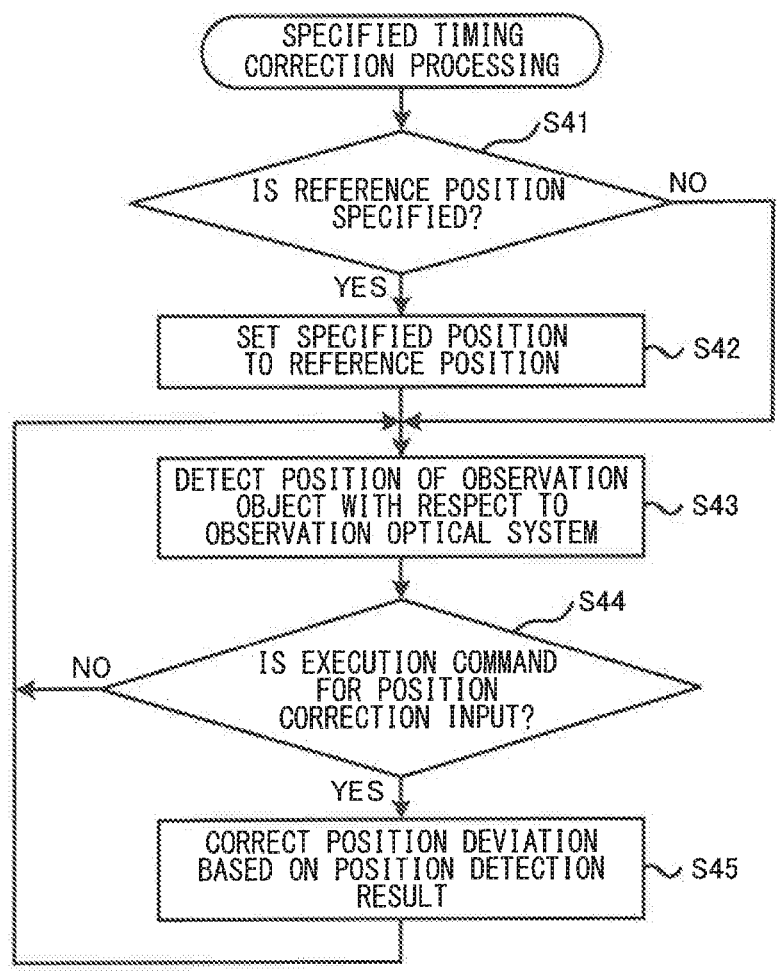
FIG. 10 is a flowchart of specified timing correction processing executed by the surgical microscope 1.

In this embodiment, the correction of the superimposed position of the supplemental image is continuously performed, even while the condition of the position correction is not satisfied, in the conditional auto-correction processing (see FIG. 6) and the specified timing correction processing (see FIG. 10). Therefore, the supplemental image can be continuously displayed in an appropriate position, regardless of whether the relative position of the observation object and the observation optical system 30 is being corrected. As a result, the user can more appropriately use the supplemental image.

Next, the CPU 51 determines whether an end command for the position correction processing has been input (S13). When the end command has not been input (NO in S13), the processing returns to S10. When the end command is input (YES in S13), the position correction processing ends.

The technology disclosed in the foregoing embodiment is merely an example. Thus, the technology illustrated in the foregoing embodiment can be modified. For example, the surgical microscope 1 illustrated in the embodiment described above is suitable for eye surgery. However, at least a portion of the technology illustrated in the foregoing embodiment can be applied to a surgical microscope that can be used in a field other than ophthalmology.

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. An ophthalmic surgical microscope comprising:
   an observation optical system configured to guide a first observation luminous flux for a right eye and a second observation luminous flux for a left eye from an observation object to an imaging device;
   an actuator configured to move a position of the observation optical system in at least a direction intersecting with the first observation luminous flux for the right eye and the second observation luminous flux for the left eye;
   a stereoscopic image display;
   a processor; and
   a memory storing computer-readable instructions, wherein the computer readable instructions, when executed by the processor, cause the ophthalmic surgical microscope to:
   (i) cause the stereoscopic image display to display a first observation image to be observed with a right eye of a user and a second observation image to be observed with a left eye of the user, on the basis of an image signal from the imaging device;
   (ii) detect a position of the observation object with respect to the observation optical system;
   (iii) determine whether a command to correct the deviation for correcting the deviation in the relative position is input; and
   (iv) only in response to determining that the command is input, correct a deviation in a relative position of the observation optical system with respect to the observation object, by causing the actuator to operate on the basis of the detected position of the observation object, wherein:
   after the deviation is corrected, steps (ii) to (iv) are repeated.

2. The ophthalmic surgical microscope according to claim 1, wherein
   correcting the deviation in the relative position includes correcting the deviation in the relative position in response to determining that the deviation in the relative position of the observation object with respect to the observation optical system exceeds an allowable range.

3. The ophthalmic surgical microscope according to claim 2, wherein
   correcting the deviation in the relative position includes changing the allowable range in accordance with a magnification of a captured image of the observation object displayed on the stereoscopic image display.

4. The ophthalmic surgical microscope according to claim 1, wherein
   the computer-readable instructions, when executed by the processor, further cause the ophthalmic surgical microscope to:
   display a supplemental image superimposed on a captured image of the observation object that is displayed on the stereoscopic image display, the supplemental image being used to assist a user with surgery on a biological object being the observation object; and
   correct a position where the supplemental image is imposed on the captured image of the observation object, on the basis of the detected position of the observation object.

5. The ophthalmic surgical microscope according to claim 1, wherein
   detecting the position of the observation object includes detecting the position of the observation object with respect to the observation optical system, by detecting a position of one of an optical element and a surgical instrument, in an image captured by the imaging device, the one of the optical element and the surgical instrument being arranged in a fixed position with respect to the observation object.

6. The ophthalmic surgical microscope according to claim 1, wherein
   the computer-readable instructions, when executed by the processor, further cause the ophthalmic surgical microscope to:
   receive an input of a command to specify a reference position, the reference position serving as a reference for correcting the deviation in the relative position, and correcting the deviation in the relative position includes correcting the deviation in the relative position, by causing the actuator to operate to bring the relative position closer to the reference position.

* * * * *